United States Patent
Corbett

(10) Patent No.: US 9,352,320 B2
(45) Date of Patent: May 31, 2016

(54) THERMAL CYCLING DEVICE WITH SELECTIVELY OPENABLE SAMPLE PORT

(75) Inventor: John Michael Corbett, Mortlake (AU)

(73) Assignee: QIAGEN INSTRUMENTS AG, Hombrechtikon (CH)

( * ) Notice: Subject to any disclaimer, the term of this patent is extended or adjusted under 35 U.S.C. 154(b) by 1131 days.

(21) Appl. No.: 12/675,659

(22) PCT Filed: Aug. 28, 2008

(86) PCT No.: PCT/AU2008/001272

§ 371 (c)(1),
(2), (4) Date: Sep. 23, 2010

(87) PCT Pub. No.: WO2009/026639

PCT Pub. Date: Mar. 5, 2009

(65) Prior Publication Data

US 2011/0008881 A1    Jan. 13, 2011

(30) Foreign Application Priority Data

Aug. 28, 2007  (AU) .............................. 2007904654

(51) Int. Cl.
| | |
|---|---|
| *B01L 1/00* | (2006.01) |
| *B01L 3/00* | (2006.01) |
| *B01L 7/00* | (2006.01) |
| *C12Q 1/68* | (2006.01) |
| *G01N 35/00* | (2006.01) |

(52) U.S. Cl.
CPC ................ *B01L 7/52* (2013.01); *C12Q 1/6844* (2013.01); *B01L 2300/046* (2013.01); *B01L 2300/0609* (2013.01); *B01L 2300/0803* (2013.01); *B01L 2300/1805* (2013.01); *G01N 35/0099* (2013.01); *G01N 2035/00366* (2013.01)

(58) Field of Classification Search
CPC ... B01L 2200/18; B01L 2200/16; B01L 9/50; B01L 7/52; B01L 2300/046
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,800,159 A | 1/1989 | Mullis et al. | |
| 4,889,818 A | 12/1989 | Gelfand et al. | |
| 4,965,188 A | 10/1990 | Mullis et al. | |
| 5,005,981 A * | 4/1991 | Schulte et al. | ................. 366/219 |
| 5,023,171 A | 6/1991 | Ho et al. | |
| 5,066,584 A | 11/1991 | Gyllensten et al. | |
| 5,075,216 A | 12/1991 | Innis et al. | |

(Continued)

FOREIGN PATENT DOCUMENTS

| | | | |
|---|---|---|---|
| EP | 0377505 | A2 | 7/1990 |
| EP | 0458138 | A2 | 11/1991 |

(Continued)

OTHER PUBLICATIONS

International Search Report dated Nov. 14, 2009.

*Primary Examiner* — Nathan Bowers

(74) *Attorney, Agent, or Firm* — McBee Moore Woodward & Vanik IP, LLC

(57) ABSTRACT

A device for thermal cycling a plurality of samples, the device including a chamber for housing a plurality of sample containers, the chamber having a selectively openable port, wherein one or more selected sample containers can be introduced to or withdrawn from the chamber through the port during thermal cycling.

21 Claims, 13 Drawing Sheets

(56) References Cited

U.S. PATENT DOCUMENTS

| | | | |
|---|---|---|---|
| 5,079,352 A | 1/1992 | Gelfand et al. | |
| 5,091,310 A | 2/1992 | Innis | |
| 5,104,792 A | 4/1992 | Silver et al. | |
| 5,281,516 A | 1/1994 | Stapleton et al. | |
| 5,447,690 A | 9/1995 | Sugaya | |
| 5,510,082 A | 4/1996 | Arai et al. | |
| 5,601,141 A | 2/1997 | Gordon et al. | |
| 6,055,050 A * | 4/2000 | Skiffington | 356/244 |
| 6,228,636 B1 * | 5/2001 | Yahiro et al. | 435/303.1 |
| 6,337,435 B1 | 1/2002 | Chu et al. | |
| 6,558,947 B1 | 5/2003 | Lund et al. | |
| 7,745,205 B2 * | 6/2010 | Wittwer et al. | 435/287.2 |
| 9,085,413 B2 * | 7/2015 | Rosmarin | G01N 35/0099 |
| 9,164,113 B2 * | 10/2015 | Friedman | G01N 35/0099 |
| 2003/0138940 A1 * | 7/2003 | Lemmo et al. | 435/287.1 |
| 2005/0002828 A1 * | 1/2005 | Gunji | B01L 3/0217 422/400 |
| 2005/0064582 A1 * | 3/2005 | Wittwer et al. | 435/287.2 |
| 2007/0065936 A1 * | 3/2007 | Hasegawa et al. | 435/288.7 |
| 2008/0268528 A1 * | 10/2008 | Ammann et al. | 435/287.2 |
| 2011/0042582 A1 * | 2/2011 | Ingber | G01N 21/0303 250/458.1 |

FOREIGN PATENT DOCUMENTS

| | | |
|---|---|---|
| EP | 0679896 A1 | 11/1995 |
| GB | 2394276 A | 4/2004 |
| WO | 92/14550 | 9/1992 |

* cited by examiner

THERMAL CYCLING DEVICE WITH SELECTIVELY OPENABLE SAMPLE PORT

CROSS REFERENCE TO RELATED APPLICATIONS

This application is a §371 National Stage Application of PCT/AU2008/001272 filed Aug. 28, 2008, which claims priority to Australian Application 2007904654 filed Aug. 28, 2007.

FIELD OF THE INVENTION

The present invention relates to thermal cycling devices and in particular to thermal cycling devices for nucleic acid amplification. However, it will be appreciated that the invention is not limited to this particular field of use.

DESCRIPTION OF THE BACKGROUND ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

Polymerase Chain Reaction (PCR) is a technique involving multiple cycles that results in the exponential amplification of certain polynucleotide sequences each time a cycle is completed. The technique of PCR is well known and is described in many books, including, PCR: A Practical Approach M. J. McPherson, et al., IRL Press (1991), PCR Protocols: A Guide to Methods and Applications by Innis, et al., Academic Press (1990), and PCR Technology: Principals and Applications for DNA Amplification H. A. Erlich, Stockton Press (1989). PCR is also described in many US patents, including U.S. Pat. Nos. 4,683,195; 4,683,202; 4,800,159; 4,965,188; 4,889,818; 5,075,216; 5,079,352; 5,104,792; 5,023,171; 5,091,310; and 5,066,584.

The PCR technique typically involves the step of denaturing a polynucleotide, followed by the step of annealing at least a pair of primer oligonucleotides to the denatured polynucleotide, i.e., hybridizing the primer to the denatured polynucleotide template. After the annealing step, an enzyme with polymerase activity catalyzes synthesis of a new polynucleotide strand that incorporates the primer oligonucleotide and uses the original denatured polynucleotide as a synthesis template. This series of steps (denaturation, primer annealing, and primer extension) constitutes a PCR cycle.

As cycles are repeated, the amount of newly synthesized polynucleotide increases exponentially because the newly synthesized polynucleotides from an earlier cycle can serve as templates for synthesis in subsequent cycles. Primer oligonucleotides are typically selected in pairs that can anneal to opposite strands of a given double-stranded polynucleotide sequence so that the region between the two annealing sites is amplified.

Denaturation of DNA typically takes place at around 90 to 95° C., annealing a primer to the denatured DNA is typically performed at around 40 to 60° C., and the step of extending the annealed primers with a polymerase is typically performed at around 70 to 75° C. Therefore, during a PCR cycle the temperature of the reaction mixture must be varied, and varied many times during a multicycle PCR experiment.

The PCR technique has a wide variety of biological applications, including for example, DNA sequence analysis, probe generation, cloning of nucleic acid sequences, site-directed mutagenesis, detection of genetic mutations, diagnoses of viral infections, molecular "fingerprinting" and the monitoring of contaminating microorganisms in biological fluids and other sources.

In addition to PCR, other in vitro amplification procedures, including ligase chain reaction as disclosed in U.S. Pat. No. 4,988,617 to Landegren and Hood, have also been developed. More generally, several important methods known in the biotechnology arts, such as nucleic acid hybridization and sequencing, are dependent upon changing the temperature of solutions containing sample molecules in a controlled fashion.

Conventional techniques including PCR typically rely on the use of individual wells or tubes cycled through different temperature zones. For example, a number of thermal "cyclers" used for DNA amplification and sequencing reactions have been described in which a temperature controlled element or "block" holds a reaction mixture, and wherein the temperature of the block is varied over time. Whilst a relatively large number of samples can be processed simultaneously with such devices (e.g. 96 well plates are commonly employed), such devices suffer various drawbacks, in that they are relatively slow in cycling the reaction mixtures, temperature control is less than ideal and detection of the reaction mixture in situ is difficult. Also, such blocks only allow for a "batch" mode of operation since the entire block is simultaneously cooled and heated. Further, it will be appreciated that since it is relatively inconvenient to operate the block if there are only a few samples to run, operators of such devices typically prefer to wait until they have sufficient samples to occupy the majority of the available sample positions, meaning that any urgent samples must wait. Further still, if the temperature cycling routine is started, any vacant positions typically cannot be utilized until the thermal cycling routine is complete and any urgent samples must again wait until the cycle is complete.

In an effort to avoid several of these disadvantages, recent advances have seen the development of block thermal cyclers providing the simultaneous running of different temperature profiles, e.g. as disclosed in U.S. Pat. No. 5,601,141 and U.S. Pat. No. 6,558,947. However, these thermocyclers suffer their own drawbacks. For example, they are relatively expensive and complex, require constant routine maintenance, temperature control is less than ideal and detection of the reaction(s) occurring the reaction containers is still difficult.

Thus, there still remains a need for thermocyclers for PCR which provide accurate temperature control of the reaction mixtures, are not complex to use, can provide real-time analysis of the reaction occurring in the sample containers, and which can operate in a batch or a continuous mode whereby samples can be continuously added and/or removed from the thermocycler during cycling without thermally affecting samples which have only received part of the required number of thermal cycles.

The present invention seeks to overcome or ameliorate at least one of the disadvantages of the abovementioned arrangements, or to provide an alternative to existing arrangements.

SUMMARY OF THE INVENTION

According to a first aspect there is provided herein a device for thermal cycling a plurality of samples, the device including a chamber for housing a plurality of sample containers, the chamber having a selectively openable port, wherein one or more selected sample containers can be introduced to or withdrawn from the chamber through the port during thermal cycling.

In an embodiment the introduction or withdrawal of the one or more selected sample containers has a minimal effect on the temperature or thermal uniformity of the plurality of sample containers during thermal cycling.

In an embodiment the port is sized such that when in an open position, the chamber is not substantially open to the ambient atmosphere. In an embodiment the port in the open position defines an aperture, the aperture being relatively small compared to an internal surface area of the chamber.

In an embodiment a gripping device is used to introduce or withdraw the one or more selected sample containers. In an embodiment the port is in an open position for a minimal time to allow the gripping device to introduce or withdraw the one or more sample containers. The gripping device may be sized and shaped such that the gripping device has a close fitting relationship with an aperture defined by the port in the open position. Further, an outer periphery of the port may have a rubber seal and an outer diameter of the gripping device may be sized to provide an air-tight seal when the gripping device is at least partially inserted therethrough. The gripping device may include a flange, the flange being configured to seal against the port when the gripping device is at least partially inserted therethrough. The gripping device may be substantially cylindrical in shape and the port has a circular opening.

In an embodiment the plurality of sample containers are supported on a platform housed in the chamber. The platform may be a rotatable carousel rotatably mounted within the chamber.

In an embodiment the thermal cycling is configured for nucleic acid amplification.

In an embodiment the plurality of sample containers are configured for relatively rapid thermal equilibration and to allow for detection of the reaction mixture. The plurality of sample containers may be formed from glass or plastic materials or a combination thereof. In an embodiment the sample containers are tubes.

In an embodiment a plurality of connected sample containers may be introduced to or withdrawn from the chamber simultaneously. The plurality of connected sample containers may be physically connected, for example forming part of a clip. A clip may comprise any number of individual sample containers, for example 2, 3, 4, 5, 6, 7, 8, 9, 10 or more sample containers.

In an embodiment the device includes an elevating device for at least partially elevating the selected container(s) enabling a gripping device to grip the selected container(s).

According to a second aspect there is provided herein a method for introducing one or more selected sample containers into, or withdrawing one or more selected sample containers from a chamber of a device in which a plurality of sample containers are being substantially uniformly thermally cycled, the chamber having a selectively openable port, the method including the steps of:
  optionally temporarily halting the thermal cycle and maintaining the temperature;
  opening the selectively openable port;
  introducing or withdrawing the selected sample container(s) to or from the chamber through the opened port;
  closing the port; and
  continuing the thermal cycle if temporarily halted.

The selected sample container(s) may be introduced or withdrawn without substantially affecting the temperature or thermal uniformity of the plurality of sample containers undergoing thermal cycling.

According to a third aspect there is provided herein a method for performing thermal cycling of a plurality of samples in a device, the device having a chamber for housing a plurality of sample containers, the chamber having a selectively openable port, the method including the step of introducing to or withdrawing from the chamber one or more selected sample containers through the port during thermal cycling.

In an embodiment the method is carried out with the device according to the first aspect.

According to a fourth aspect there is provided herein a method for performing sequential thermal cycling of a plurality of samples, the method including the steps of:
  introducing a plurality of sample containers into a device, the device having a chamber for housing the plurality of sample containers, the chamber having a selectively openable port;
  initiating thermal cycling; and,
  introducing or withdrawing from the chamber one or more selected sample containers through the port during thermal cycling.

According to a fifth aspect there is provided herein a method for performing thermal cycling of a plurality of samples being substantially uniformly thermally cycled in a chamber having a selectively openable port, the method including the steps of:
  opening the selectively openable port; and
  introducing to or withdrawing from the chamber one or more sample containers during thermal cycling, such that an effect on temperature or thermal uniformity of the chamber is minimised.

According to a sixth aspect there is provided herein a method for performing thermal cycling of a plurality of samples being substantially uniformly thermally cycled in a chamber having a selectively openable port, the method including the steps of:
  optionally temporarily halting the thermal cycle and maintaining temperature of the chamber;
  opening the selectively openable port;
  introducing to or withdrawing from the chamber, one or more sample containers through the opened port;
  closing the port; and,
  continuing the thermal cycle if temporarily halted, wherein introducing to or withdrawing from the chamber one or more sample containers has minimal effect of temperature or thermal uniformity of the plurality of samples.

Also disclosed herein is a device for introducing or withdrawing a sample container to or from a plurality of sample containers being substantially uniformly thermally cycled, the device comprising a chamber for housing said plurality of sample containers, the chamber having a selectively openable port for admitting a gripping device for introducing or withdrawing said sample container without substantially affecting the temperature or thermal uniformity of the plurality of sample containers during the thermal cycling.

Also disclosed herein is a method for introducing or withdrawing a sample container to or from a plurality of sample containers being substantially uniformly thermally cycled in a chamber having a selectively openable port, the method comprising the steps of: opening the selectively openable port; and introducing or withdrawing the sample container to or from said plurality of sample containers during the thermal cycling without substantially affecting the temperature or thermal uniformity of said plurality of sample containers. The sample container may be introduced or withdrawn using a gripping device. Typically the selectively openable port is closed after the sample container is introduced or withdrawn from the chamber.

In accordance with the aspects and embodiments described herein, it will be appreciated that in order to minimise the effect of the process of introducing or withdrawing a sample container to or from the chamber on any pre-existing sample containers which may have only partially received their required number of thermal cycles, the selectively openable port may be sized such that, when in its open position, the chamber is not substantially open to the ambient atmosphere. In other words, the aperture defined by the port in its opened position is relatively small compared to the internal surface area of the chamber housing the plurality of sample containers undergoing thermal cycling. Accordingly, any loss of heating or cooling fluid from the chamber resulting from opening the port is small or negligible so as to have minimal effect on any pre-existing sample containers. Typically the heating and cooling means providing the thermal cycling have sufficient capacity such that they can accommodate for any loss of fluid from the chamber through the opened port such that the temperature in the chamber remains at the desired or predetermined level, and more importantly that the temperature of any existing samples is not substantially affected. Typically the heating/cooling fluid is air but could be other fluids as is well known in the art. Furthermore, the selectively openable port is, according to one embodiment, adapted to be in the open position for the minimum time necessary to allow the gripping device to introduce or withdraw a sample container to or from the chamber.

In an embodiment, the gripping device is sized and shaped so as to be in close fitting relationship with the aperture defined by the port in its open position to minimise ingress/egress of fluid to/from the chamber. In other embodiments a rubber seal may be provided around the periphery of the port and the outer diameter of the gripping device may be sized so as to provide an air-tight seal. In yet another embodiment, a flange may also be provided on the gripping device so as to provide a seal with the port. Additionally, the gripping device may be substantially right cylindrical in shape and the port is circular. However, the skilled person will appreciate that other shapes and configurations will be possible without departing from the spirit and the scope of the invention.

According to further embodiments, the plurality of sample containers may be supported on a platform housed in the chamber adapted to be heated or cooled for providing the thermal cycling, for example for conducting nucleic acid amplification (e.g. PCR). The platform is in one particular embodiment, a rotatable carousel rotatably mounted within the chamber, and is adapted to receive the sample containers in slots or apertures. The chamber typically includes drive means for driving the rotatable carousel thereby applying a centrifugal force to the sample containers during cycling for maintaining the reaction mixture at the base of the sample container. Examples of thermocyclers for use in accordance with the present invention include the Rotor-Gene™ family of thermocyclers manufactured and distributed by Corbett Life Sciences Pty Limited (www.corbettlifescience.com). Other similar devices are disclosed in WO 92/20778 and WO 98/49340. However, it will be appreciated that other commercially available thermocyclers may be modified as described herein. Notably, the Rotor-Gene™ family of thermocyclers are of particular applicability as they provide identical container-to-container conditions, excellent thermal control of the samples undergoing thermal cycling, and real-time analysis of the reaction mixtures. This is achieved, in part, by use of a rotor, the design of the heating and cooling systems and the associated optics for providing real-time analysis of the PCR reaction. The fact that samples are spinning ensures that all samples are heated and cooled at the same rate. Consequently, no equilibration times are required when a set point is reached.

For use in accordance with the present invention, sample containers are typically adapted for relatively rapid thermal equilibration and to allow for detection of the reaction mixture, and may be formed from glass or plastics materials. For example the sample containers may be Eppendorf tubes. Any reaction mixture may be included into the sample containers however in the examples contemplated herein the reaction mixtures are for nucleic acid amplification and the theremocycler configured accordingly, i.e. the thermal cycling routine is particularly adapted for nucleic acid amplification as discussed above.

In an embodiment the gripping device introduces or withdraws the sample container from its seat/support on the carousel in a substantially axial motion with respect to the sample container. However, it will be appreciated that the gripping device may clip the sample container in and out from the side of the rotor, or the sample container may be introduced/withdrawn from underneath the rotor. However, the actual mode of introduction or withdrawal is less important than being able to introduce or withdraw a sample container during thermal cycling and without thermally disturbing any pre-existing samples.

The skilled addressee will appreciate that the aspects and embodiments described herein, in addition to enabling the thermal cycling of samples in a batch-processing mode, can also enable a "continuous" mode of operation whereby new samples may be added to a set of samples which are part-way through receiving a predetermined number of thermal cycles. This continuous mode means that there is now no need for an operator to wait for the batch to be complete since completed samples (i.e. samples which have had the requisite number of thermal cycles) can be withdrawn from the chamber at regular intervals corresponding with their time of introduction to the chamber, thereby allowing the remaining samples to continue cycling and simultaneously freeing up a position for the introduction of a new sample. Further, thermal cycling can be begun with only a small number of samples, with the flexibility of being able to introduce additional samples at a later stage. For examples, the aspects and embodiments described herein make it possible to analyze samples on an urgent basis, as may be required for example in the field of medical diagnostics, without the need for either an existing thermal cycling batch to finish or an entire device to become available.

It will be appreciated by the skilled addressee that when operating centrifugal-type devices the issue of balancing samples need to be considered. For example, in the case of high velocity rotation devices this is typically accommodated by including diametrically opposed sample containers having the same weight. However, in the case of PCR, since the amount of material is usually very small typically no balancing issues present themselves. Furthermore, under relatively slow rotation, such as 400 to 1000 RPM, balancing is less of an issue. With high speed rotation devices or when using large sample volumes, the device may be configured to take such balancing issues into account by ensuring that diametrically opposed counterweights are introduced/withdrawn together with the selected sample container(s), or by ensuring that that samples are added or removed in diametrically opposed pairs.

It will also be appreciated by the skilled addressee that during a continuous mode of operation, in the case of rotor-based devices and PCR-based reactions the rotor is typically temporarily stopped from rotation during the anneal stage of the thermal cycle (i.e. temperatures of 40 to 60° C.), and optionally the temperature temporarily held constant, to allow for the selected sample container introduction/withdrawal. The rotor may then be indexed via computer control to the sample container position which is scheduled for withdrawal, or indexed to a vacant position to introduce a fresh sample container. The skilled addressee will appreciate that samples may be introduced or withdrawn not only at the anneal stage of a PCR-based thermal cycle but also at either the denature or extension stage with similar effect (i.e. 90 to 95° C. or 70 to 75° C. respectively). However to ensure that every sample receives an identical thermal history, typically sample containers are introduced to or withdrawn from the chamber at the identical point on the thermal cycling routine, thereby allowing a continuous duty cycle for a thermocycler modified in accordance with the aspects and embodiments described herein. The selectively openable port may then be opened for access to the sample containers and after one or more samples (having had their requisite number of thermal cycles) are withdrawn and/or one or more new samples introduced the port is closed and the rotor is again spun at its predetermined speed. If the thermal cycling routine was temporarily halted to allow for the introduction/withdrawal then it may be allowed to continue at this time. Notably, the reactions occurring in the sample containers may also be continuously analyzed before, during and after sample container introduction and/or withdrawal.

Also disclosed herein is a method for introducing one or more selected sample containers into a chamber or withdrawing one or more selected sample containers from a chamber wherein a plurality of sample containers are supported on a rotatable carousel and being substantially uniformly thermally cycled in the chamber, the chamber having a selectively openable port and the rotatable carousel being rotated in the chamber, the method comprising the steps of:

optionally temporarily halting the thermal cycle and maintaining the temperature;
stopping rotation of the carousel and indexing either to a sample container requiring withdrawal or a vacant position on the carousel for receiving the sample container;
opening the selectively openable port;
introducing or withdrawing the one or more selected sample containers through the opened port;
closing the port;
continuing rotation of the carousel; and
continuing the thermal cycle if temporarily halted.

The selected sample container(s) may be introduced or withdrawn without substantially affecting the temperature or thermal uniformity of the plurality of sample containers.

In accordance with the aspects and embodiments described herein a computer controlled robotic arm having said gripping device at its distal end can be used to automatically introduce or withdraw the sample containers from the chamber. For example, the sample containers can be assembled on a rack and an operator can program the software operating both the thermocycler and the robotic arm to obtain the sample containers from the rack in a predetermined order and introduce them into the chamber, optionally during a thermal hold as described above. The software can then proceed to count the number of thermal cycles that sample container receives and automatically withdraws the container once a predetermined number of cycles is reached and replaces the container on the rack, optionally introducing a new sample container from the rack into the carousel position which has just been vacated. It will be appreciated that if insufficient samples are available to fill the available positions on the rotor the thermocycler can continue the thermal cycling process until the samples have received the required number of cycles and then withdraw the samples automatically. Further, it will be appreciated that if the rotor is full then new samples may be queued and introduced to the chamber when positions become available. It will further be appreciated that in the case of the urgent analysis of samples they can be introduced into the chamber as soon as positions in the chamber become available.

It will be appreciated that a device as described herein can provide for both a batch mode of operation or a continuous mode. In batch mode, all positions in the chamber may be loaded, cycled for, e.g., 40 cycles, whilst acquiring data on the reactions occurring in the sample containers. All containers may then be removed and a new batch of sample containers introduced. Alternatively, the continuous mode as described above could be implemented.

As also described herein, an elevating device may be provided for at least partially elevating a sample container from its support in the chamber to assist a gripping device in gripping the sample container. In this example, an actuator may be provided underneath the rotor and in line with the selectively openable port.

In the context of PCR-based reactions, a sample may be loaded into a sample container with an oil overlay and heated to 95° C. for a predetermined time by exposing the container to a separate 95° C. heating block to denature the sample prior to introducing the sample container into the chamber of the thermocycler. Where a rotor-based thermocycler is used, in one embodiment, at the completion of this initial denaturing step software controlling the thermocycler may automatically slow the rotor and index it to the next available position in the rotor, allowing introduction of the denatured sample. Notably, any completed samples can also be withdrawn at this stage. Subsequent samples can then be introduced at the identical point in the thermal profile so that every sample receives the same thermal treatment.

It will be appreciated that any of the above forms, examples, aspects and embodiments can be implemented individually or in combination.

BRIEF DESCRIPTION OF THE DRAWINGS

Embodiments of devices and methods as described herein will now be described, by way of example only, with reference to the accompanying drawings in which.

MODES FOR CARRYING OUT THE INVENTION

Figure 1:
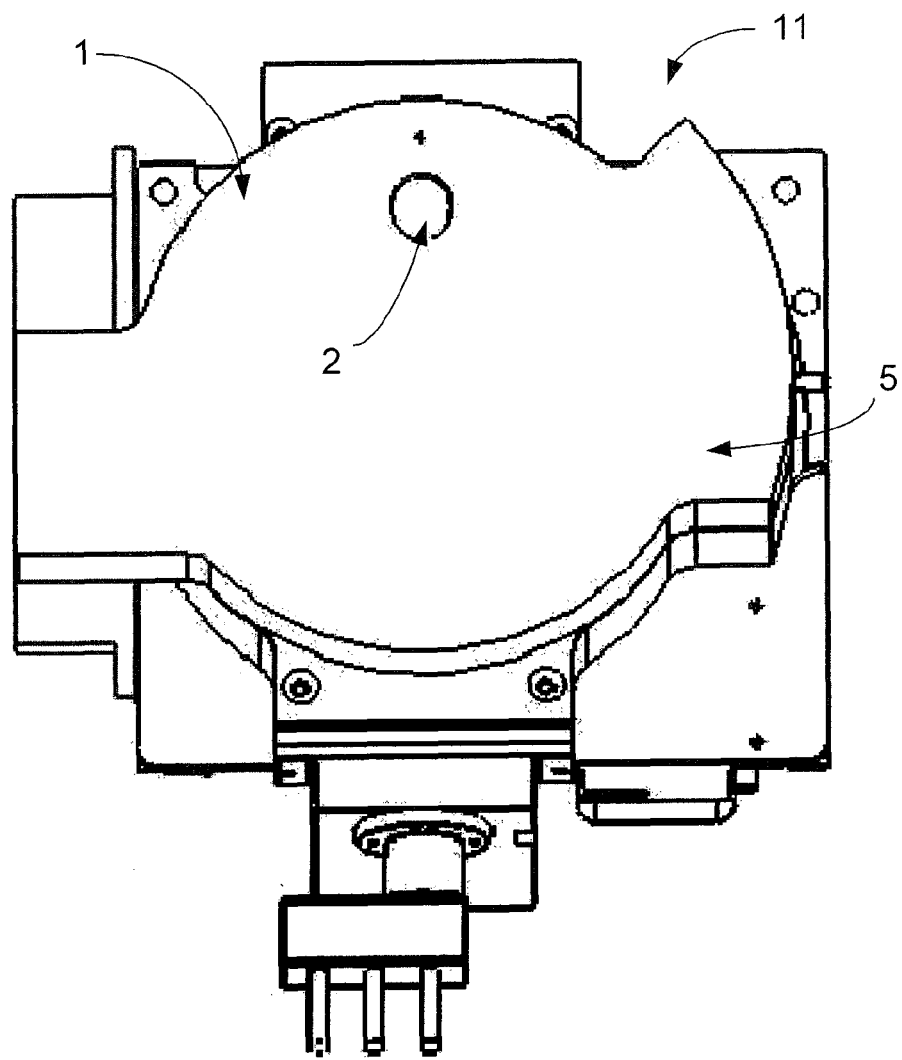
FIG. 1 is a top view of a chamber according to the invention showing a selectively openable port in its closed position.

References will now be made to the drawings, wherein like reference numerals refer to like parts throughout.

Referring initially to FIG. 1, a device 11 for thermal cycling a plurality of samples is shown.

In this particular example, the device 11 includes a chamber 1 for housing a plurality of sample containers (which are further described below) and having a top cover 5. The chamber 1 has a selectively openable port 2, where one or more selected sample containers can be introduced to or withdrawn from the chamber 1 through the port 2 during thermal cycling.

It will be appreciated that in one particular example, the introduction or withdrawal of the one or more selected sample containers has a minimal effect on the temperature or thermal uniformity of the plurality of sample containers during thermal cycling. Furthermore, the port 2 can be sized such that when in an open position, the chamber 1 is not substantially open to the ambient atmosphere.

Referring now to FIGS. 1 to 11, a chamber 1 for housing a plurality of sample containers (not shown) is provided. The chamber 1 includes a selectively openable port 2 for admitting a gripping device 3 for introducing or withdrawing a sample container 4 in the form of an tube, which in this particular example, can be an Eppendorf tube or the like, into or from the chamber without substantially affecting and/or minimising the effect on the temperature or thermal uniformity of the plurality of sample containers undergoing thermal cycling.

Figure 2:
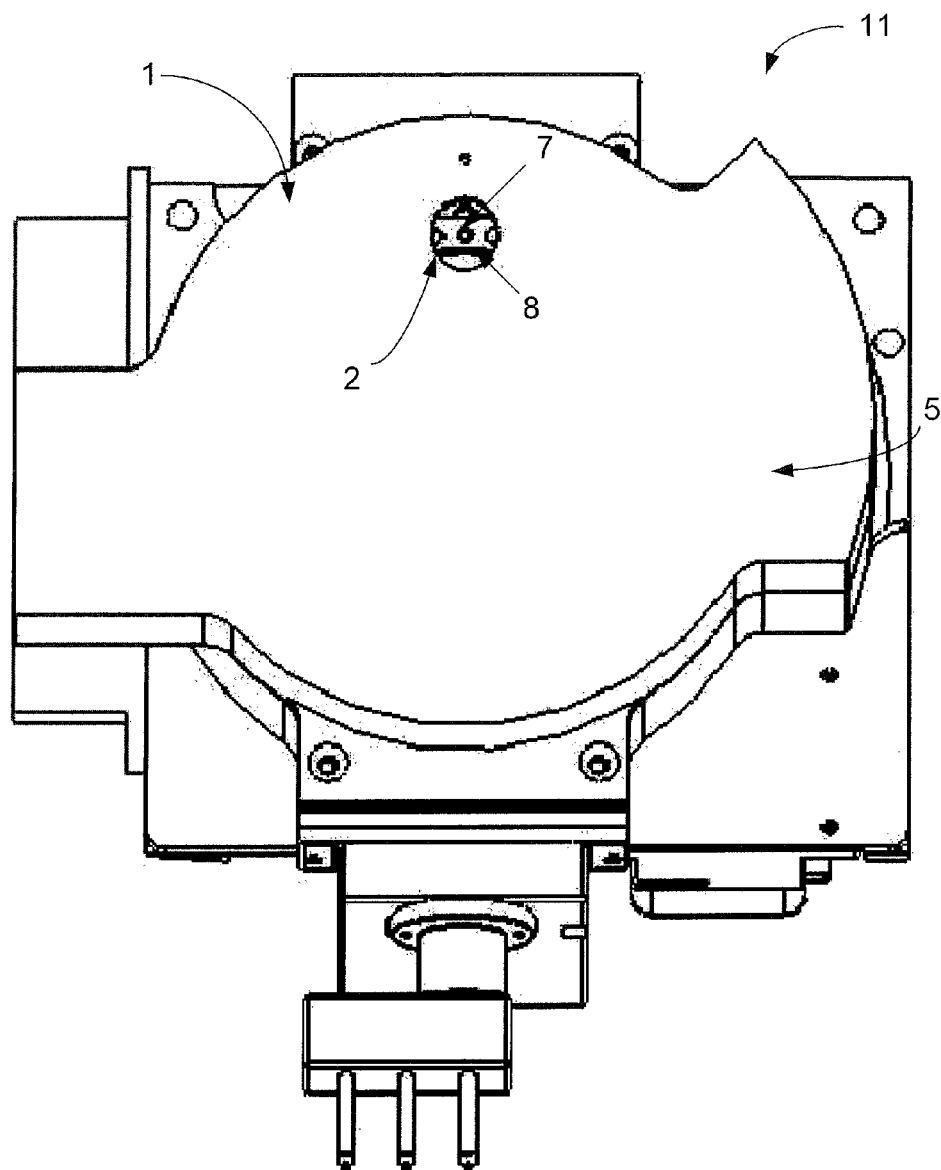
FIG. 2 is a view similar to FIG. 1, showing the port in its open position.

The selectively openable port 2 may be typically sized such that, when in its open position, as best shown in FIG. 2, the chamber 1 is not substantially open to the ambient atmosphere. Accordingly, any loss of heating or cooling air from the chamber 1 resulting from opening the port 2 is small or negligible so as to have minimal effect on the pre-existing sample containers, if any. Furthermore, the selectively openable port 2 is adapted to be in its open position for the minimum time necessary to allow the gripping device 3 to introduce or withdraw a sample container 4 into or from the chamber.

Figure 3:
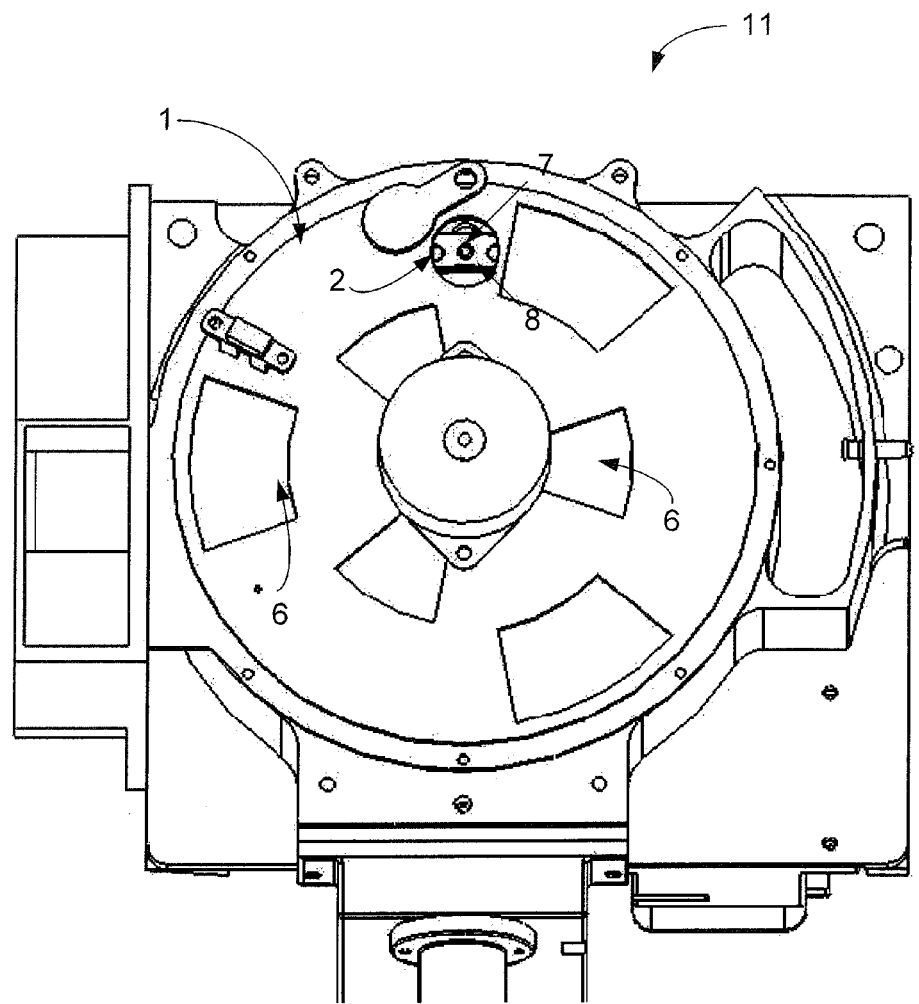
FIG. 3 is a view similar to FIG. 1, showing the top cover of the chamber removed for clarity; the port is shown in its open position and the chamber cooling ports in their closed position.
Figure 4:
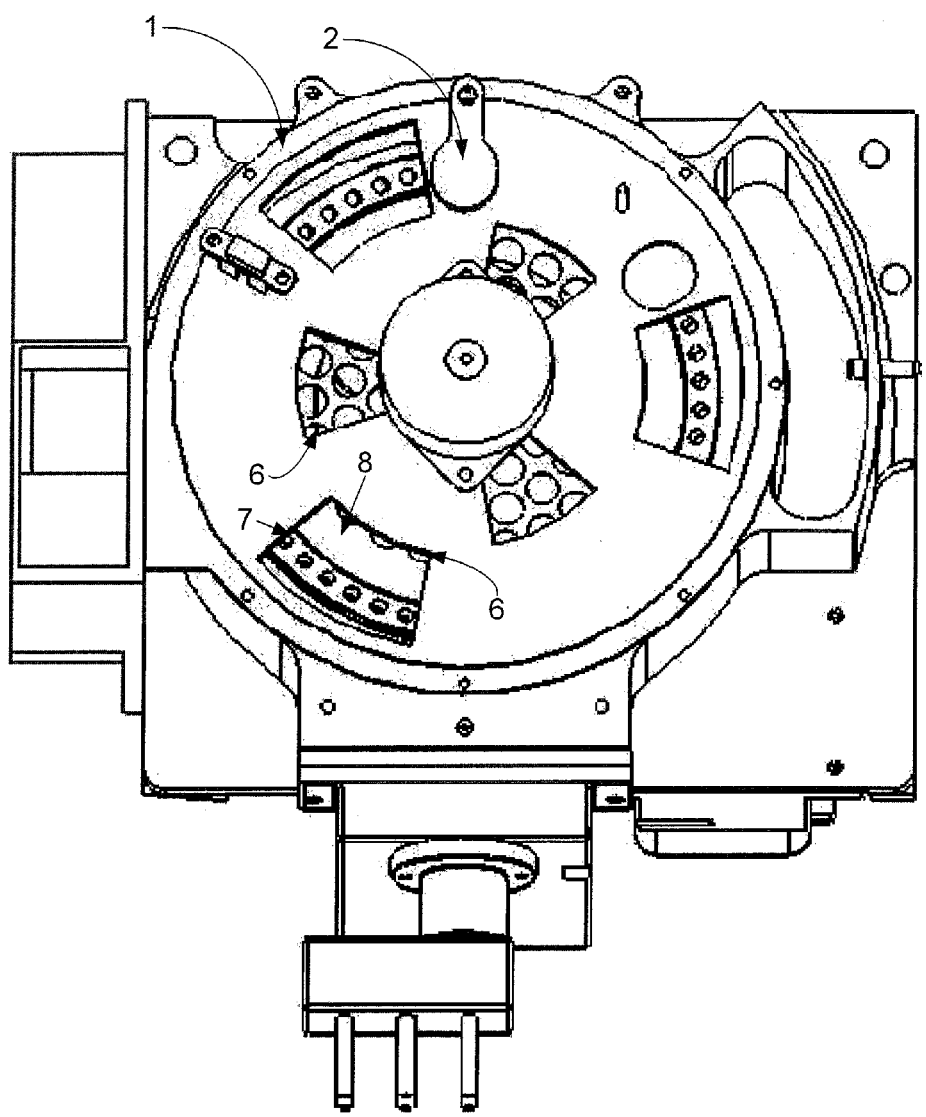
FIG. 4 is a view similar to FIG. 3, showing the port in its closed position and the chamber cooling ports in their open position.
Figure 5:
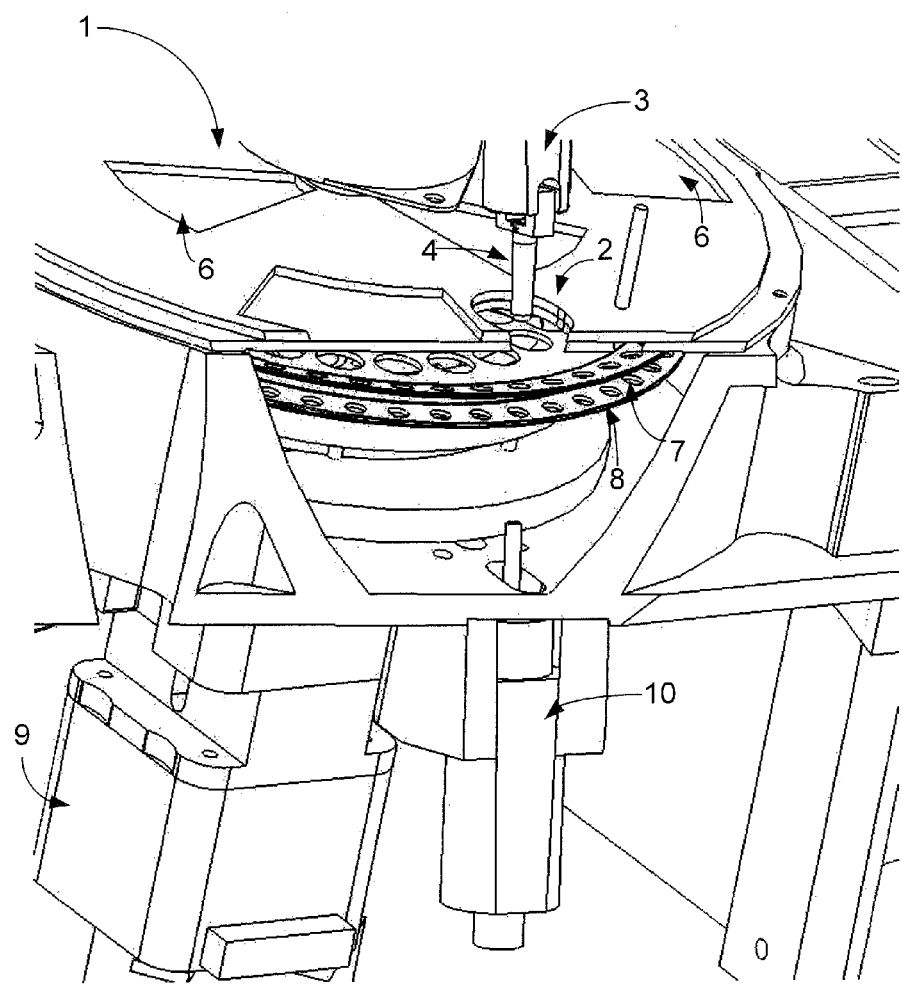
FIG. 5 is a partly cut-away perspective front view of a device according to the invention, showing the gripping device introducing a sample container into the rotor.

FIG. 3 is a plan view of the chamber 1 wherein the top cover 5 of the chamber 1 has been removed for clarity. The port 2 is shown in its open position and the chamber 1 cooling ports 6 in their closed position. FIG. 4 is a view similar to FIG. 3 but showing the port 2 in its closed position and the chamber 1 cooling ports 6 in their open position.

Figure 7:
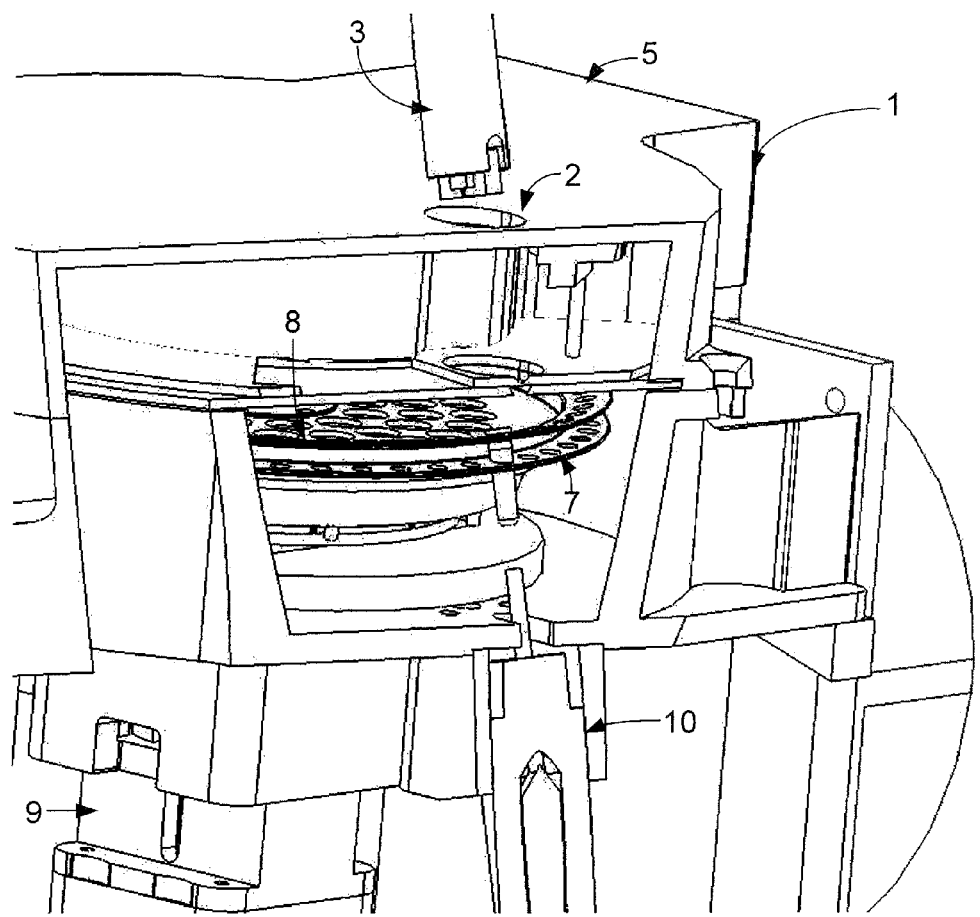
FIG. 7 is a view similar to FIG. 6, showing the gripping device moving into the chamber to withdraw the sample container.
Figure 8:
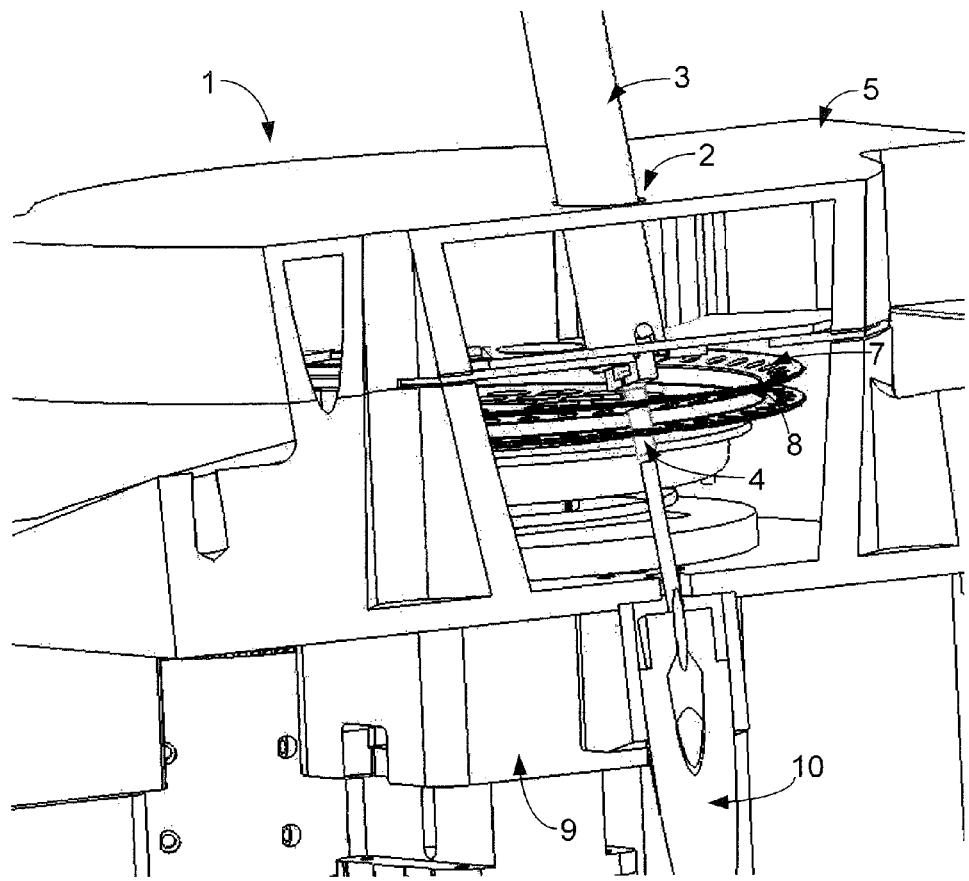
FIG. 8 is a view similar to FIG. 7, showing the elevating device pushing the sample container from below such that the sample container protrudes from the rotor sufficiently such that the gripping device can grip the sample container and withdraw it from the chamber.

The gripping device 3 is typically sized and shaped so as to be in close fitting relationship with the aperture defined by the port 2 in its open position to minimise ingress/egress of air to/from the chamber, as best shown in FIG. 8. As best shown in FIGS. 6 to 9, the gripping device 3 introduces or withdraws the sample container 4 in a substantially axial motion with respect to the sample container 4. Accordingly, the gripping device 3 may engage with an edge of a sample container such as a tube or the like.

Furthermore, the gripping device may be sized and shaped such that the gripping device 3 has a close fitting relationship with an aperture defined by the port in the open position. According to one particular example, an outer periphery of the port 2 has a rubber seal and an outer diameter of the gripping device 3 is sized so as to provide an air-tight seal when the gripping device 3 is at least partially inserted therethrough.

The gripping device 3 may also include a flange, where in one particular example, the flange is configured to seal against the port 2 when the gripping device 3 is at least partially inserted therethrough, although it is not necessary that the flange provides a seal and can only engage with the port 2. Additionally, the gripping device 3 may be substantially cylindrical in shape, where the port 2 has a circular opening to allow for insertion and withdrawal of the gripping device 3.

Notably, it will be appreciated that many other forms of gripping devices or the like for introducing or withdrawing sample containers may be employed. These include but are not limited to vacuum or magnetic devices which pull and/or push a sample container into the chamber by using different forces.

Any sample containers which may be undergoing uniform thermal cycling in the chamber 1, may be held in apertures 7 disposed at the periphery of a rotatable carousel 8 rotatably mounted within the chamber 1. Where the chamber includes a rotatable carousel the chamber further includes drive means 9 for driving the rotatable carousel 8 thereby applying a centrifugal force to the sample containers during cycling for maintaining the reaction mixture at the base of the sample container 4.

Figure 6:
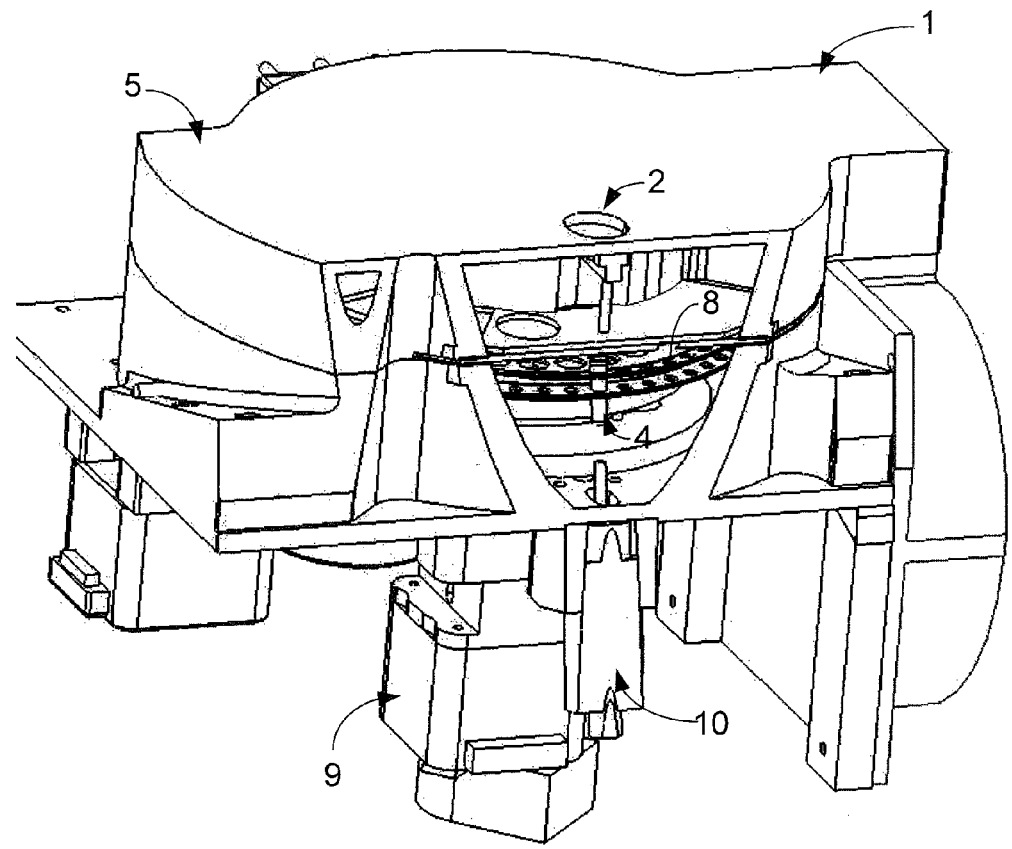
FIG. 6 is a view similar to FIG. 5, showing the sample container in the rotor at the loading/unloading position after having had a plurality of thermal cycles.
Figure 9:
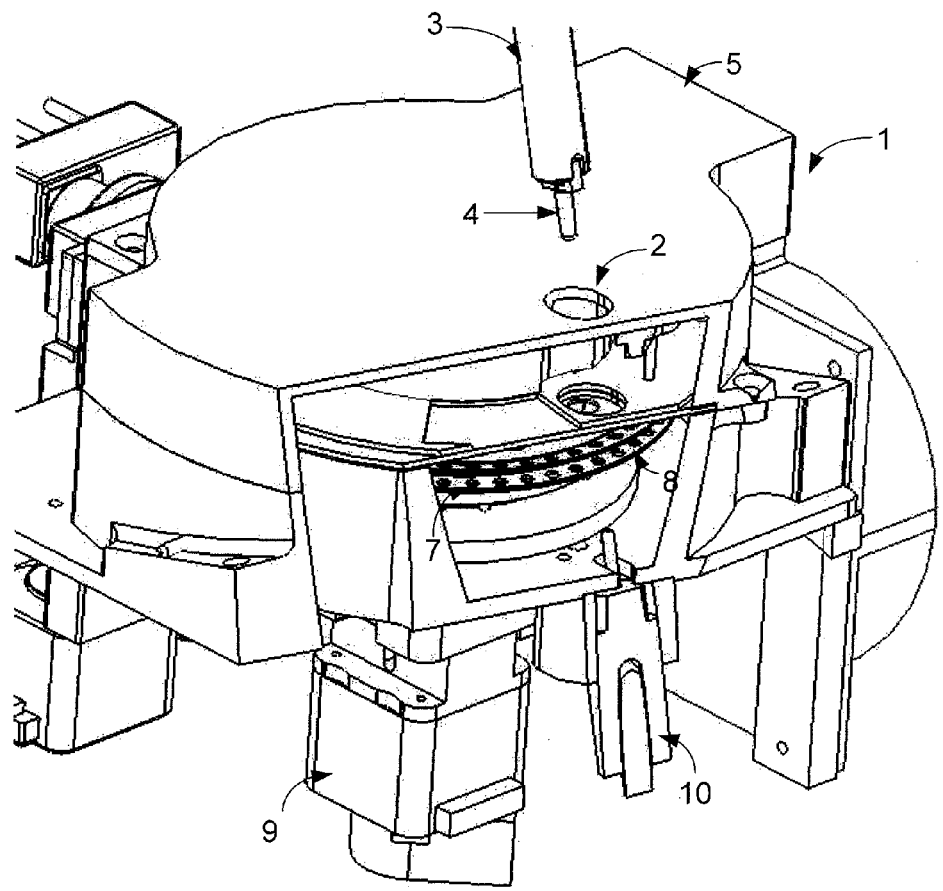
FIG. 9 is a view similar to FIG. 8, showing the sample container fully withdrawn from the chamber.
Figure 10:
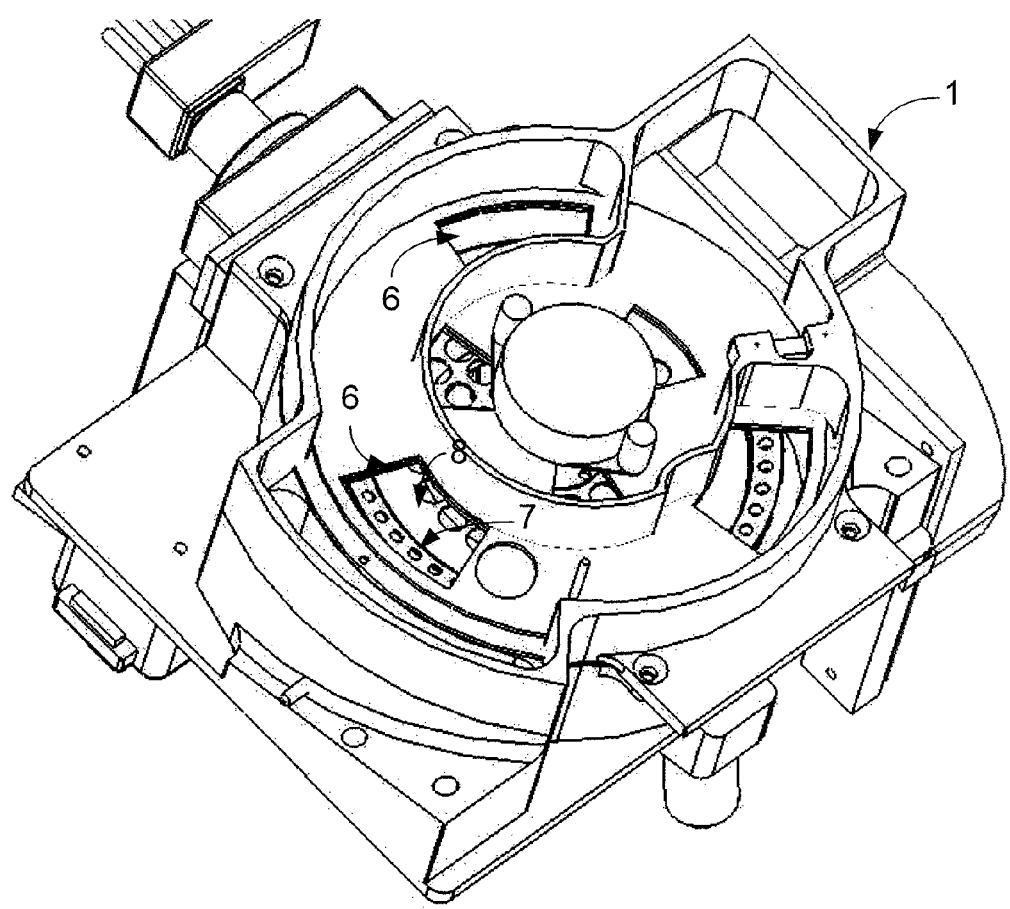
FIG. 10 is view similar to FIG. 4 in a perspective view.
Figure 11:
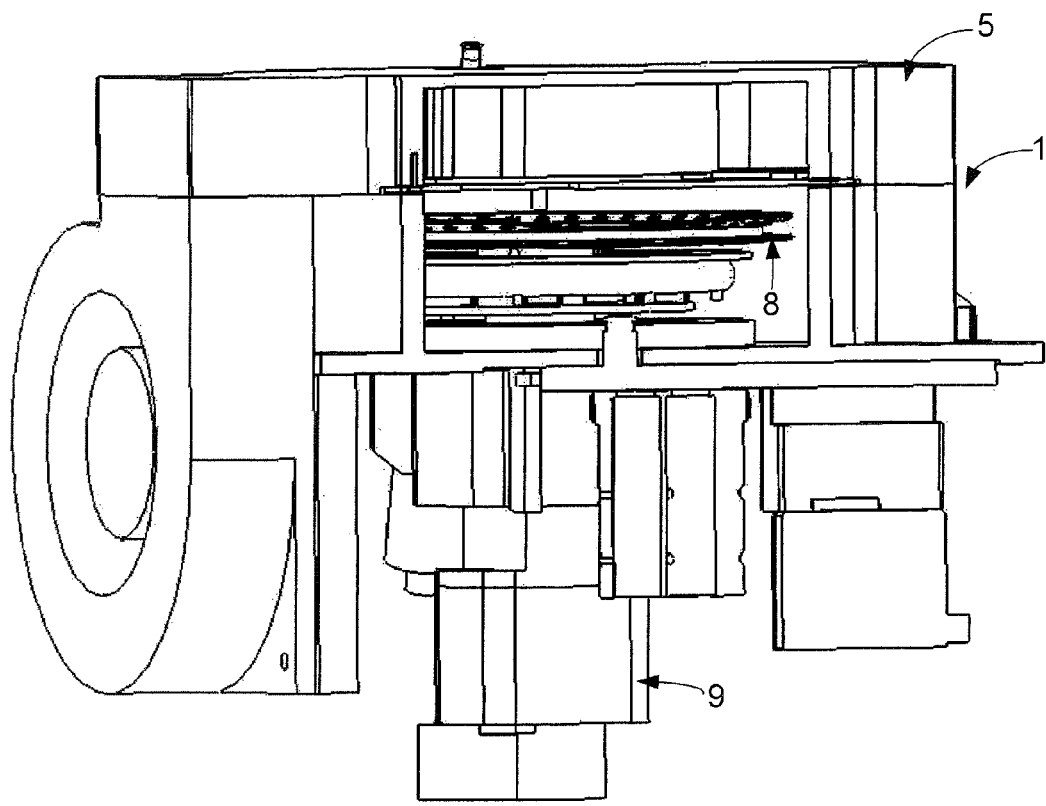
FIG. 11 is a partly cut-away side view of a device according to the invention, showing the air cooler (blower) for cooling the chamber.

Referring now to FIGS. 5 to 9, FIG. 5 shows a partly cut-away perspective front view of a device described herein, showing the gripping device 3 introducing a sample container 4 into the rotatable carousel 8. FIG. 6 is a view similar to FIG. 5 but showing the sample container 4 in the rotatable carousel 8 at the unloading position after having had a plurality of thermal cycles and ready for withdrawal. FIG. 7 is a view similar to FIG. 6 but showing the gripping device 3 moving into the chamber 1 through the opened port 2 to withdraw the sample container 4. FIG. 8 is a view similar to FIG. 7 but showing the elevating device 10 in the form of a "push pin" pushing the sample container 4 from below such that the sample container 4 protrudes from the rotatable carousel 8 sufficiently such that the gripping device 3 can grip the sample container 4 and withdraw it from the chamber 1, as best shown in FIG. 9.

In one example, a PCR sample is loaded into a sample container 4 with an oil overlay and heated to 95° C. for 2 minutes on a hot plate to activate an enzyme and denaturing the sample. The rotor is then temporarily stopped from rotation whilst the chamber is at temperatures of 40 to 60° C. The selectively openable port is then opened for access to the rotor 8 and the sample container 4 is introduced by the gripping device 3 to the rotatable carousel 8. The gripping device 3 is withdrawn, the port 2 is closed and the rotatable carousel 8 is again spun at its predetermined speed. The reaction occurring in the sample container 4 may also be continuously analyzed. At the time of the introduction of the sample container 4, any existing sample containers, which have had the requisite number of thermal cycles, can be withdrawn.

Figure 12:
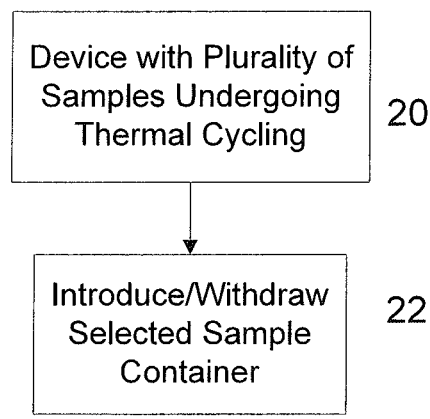
FIG. 12 is a flowchart of an example method of performing thermal cycling.

It will be appreciated that the above-described devices can be used to perform a process/method of thermal cycling. An example process of thermal cycling is shown in FIG. 12. In this particular example, as shown in FIG. 12 at step 20, whilst a plurality of samples are undergoing thermal cycling, a selected sample container can be introduced to or withdrawn from the device (at step 22).

According to another example, a method of thermal cycling can include the steps of: initiating thermal cycling in a plurality of sample containers, opening the selectively openable port 2 and introducing or withdrawing the sample container 4 to or from the chamber during thermal cycling without substantially affecting the temperature or thermal uniformity of the plurality of sample containers.

With respect to yet another example, a method of thermal cycling can also include the steps of: initiating thermal cycling in a plurality of sample containers, optionally temporarily halting the thermal cycle and maintaining the temperature, opening the selectively openable port 2 and introducing or withdrawing a sample container 4 through the opened port 2. The port 2 is then closed and the thermal cycle is continued (if temporarily halted), wherein the sample container 4 is introduced or withdrawn without substantially affecting the temperature or thermal uniformity of the plurality of sample containers.

Figure 13:
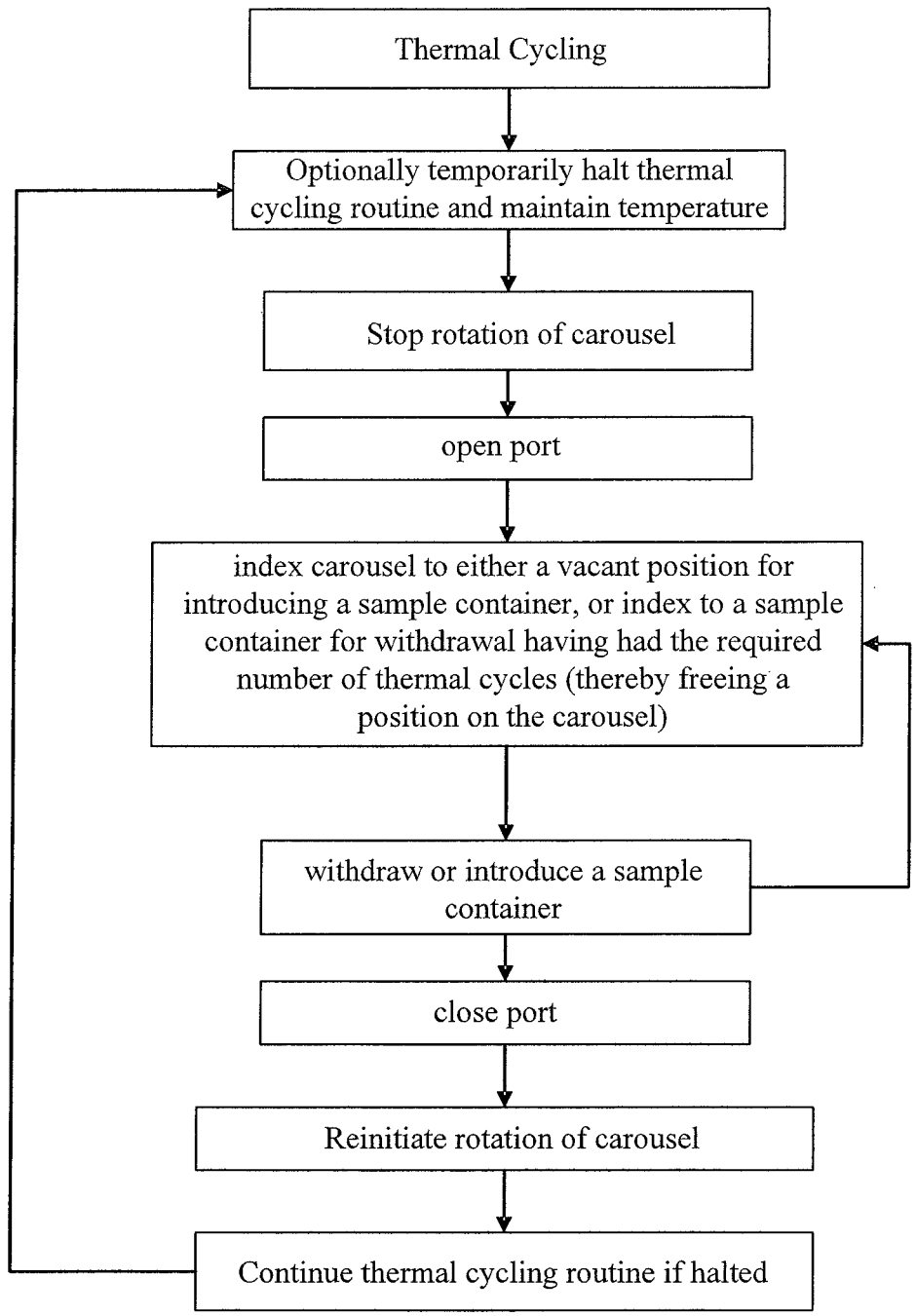
FIG. 13 is another flowchart of an example method of performing thermal cycling

Further still, a method of thermal cycling can include the steps of: initiating thermal cycling in a plurality of sample containers, optionally temporarily halting the thermal cycle and maintaining the temperature, stopping rotation of the carousel 8 and indexing either to a sample container requiring withdrawal or a vacant position on the carousel 8 for receiving a sample container 4. The selectively openable port 2 is then opened and a sample container 4 is introduced or withdrawn through the opened port, which is then closed. Rotation of the rotatable carousel 8 is then continued, as is the thermal cycle if temporarily halted, wherein the sample container 4 is introduced or withdrawn without substantially affecting the temperature or thermal uniformity of the plurality of sample containers. A flow chart of this particular example is shown in FIG. 13.

According to a further example, a method of thermal cycling in a device is provided where the device can include a plurality of sample containers supported on a rotatable carousel and being substantially uniformly thermally cycled in a chamber having a selectively openable port, where the rotatable carousel is rotated in the chamber. The method can include the steps of optionally temporarily halting the thermal cycle and maintaining the temperature; stopping rotation of the carousel and indexing either to a sample container requiring withdrawal or a vacant position on the carousel for receiving a sample container; opening the selectively openable port; introducing or withdrawing one or more selected sample containers through the opened port; closing the port; continuing rotation of the carousel; and continuing the thermal cycle if temporarily halted, wherein the sample container is introduced or withdrawn without substantially affecting and/or minimising the effect on the temperature or thermal uniformity of the plurality of sample containers.

With respect to a further example, a method for performing thermal cycling in a device is provided where the device includes a plurality of sample containers supported on a rotatable carousel and being substantially uniformly thermally cycled in a chamber having a selectively openable port, the rotatable carousel being rotated in the chamber. The method can include the steps of: optionally temporarily halting the thermal cycle and maintaining the temperature; stopping rotation of the carousel and indexing either to a sample container requiring withdrawal or a vacant position on the carousel for receiving a sample container; opening the selectively openable port; introducing or withdrawing the sample container through the opened port; closing the port; continuing rotation of the carousel; and continuing the thermal cycle if temporarily halted, wherein the sample container is introduced or withdrawn without substantially affecting and/or minimising any effect on the temperature or thermal uniformity of the plurality of sample containers.

It will be appreciated that the methods described herein may include the pre-step of thermally pre-treating a sample contained in a sample container. Furthermore, the sample may be thermally treated at 90° C. for 2 minutes, and the sample may also include an oil overlay for reducing evaporation.

It will be appreciated that a sample container may be introduced or withdrawn whilst the chamber is at any desired stage of a thermal cycling reaction. For example, a sample container may be introduced or withdrawn whilst the chamber is at a temperature of between about 40 to 60° C. The number of thermal cycles may be determined on a case by case basis, but by way of example, may be between about 20 and 50. It will further be appreciated that reactions occurring in the sample containers may be continuously analyzed during thermal cycling and that such analysis is not compromised by the employment of devices and methods as described herein. Additionally, with reference the drawings, it will also be appreciated that the sample container may be at least partially elevated during withdrawal from the chamber by any suitable means.

As used herein the term "sample containers" means any form of container adapted to include, hold, etc, a single sample. For example, as described above, the sample container is typically a tube or the like, such as an Eppendorf tube. Sample containers may be composed of any suitable materials, for example glass and/or plastic. For thermal cycling applications the tube will typically be suitable to enable efficient thermal transfer within the container and may have an optical clarity sufficient to enable real-time analysis of the sample to take place. The sample containers may be of any suitable size as will be appreciated by those skilled in the art.

Typically the opening port of the chamber is configured to collaborate with the gripping device for loading the tubes into and out of the chamber and may be adapted to be of a similar size to the maximum diameter of the sample containers.

A plurality of sample containers may be introduced to or withdrawn from the chamber simultaneously. Such sample containers may be physically connected by any suitable means. For example, a plurality of sample containers may form part of a clip. A connected plurality of sample containers may include any number of individual sample containers, such as 2, 3, 4, 5, 6, 8 or 10.

Furthermore, as has been described herein the size of the selectively openable port is such that, according to one example, the effect on the temperature or thermal uniformity of the plurality of samples within the chamber is minimised. Example sizes of the port can include 20 to 30 mm of opening. Additionally, according to yet a further example, it will be appreciated that the time taken to insert/withdraw selected sample containers may be anywhere between one second to one minute.

Further still, it will be appreciated that the above-described methods and devices for thermal cycling can be used for batch or sequential modes of operation.

Although the invention has been described with reference to specific examples, it will be appreciated by those skilled in the art that the invention may be embodied in many other forms. In particular features of any one of the various described examples may be provided in any combination in any of the other described examples.

Other than in the operating examples, or where otherwise indicated, all numbers expressing quantities of ingredients or reaction conditions used herein are to be understood as modified in all instances by the term "about". The examples are not intended to limit the scope of the invention.

The articles "a" and "an" are used herein to refer to one or to more than one (i.e., to at least one) of the grammatical object of the article. By way of example, "an element" means one element or more than one element.

The invention claimed is:

1. A device for thermal cycling a plurality of samples, comprising:
 a chamber for housing a plurality of sample containers, the chamber having a selectively openable port,
 a controller configured to control the chamber to provide denaturing and annealing heating stages of a thermal cycle to the plurality of sample containers housed in said chamber, and
 a gripping device,
wherein the port comprises a closed or open position,
wherein the port in the open position defines an aperture, the aperture being smaller than an internal surface area of the chamber,
wherein the port has a circular opening,
wherein the gripping device is used to introduce, or withdraw, one or more selected sample containers to or from the chamber through the port during thermal cycling, and
wherein the gripping device is sized and shaped such that the gripping device fits through the aperture defined by the port in the open position.

2. The device of claim 1, wherein the port is sized such that when in the open position, the chamber is otherwise closed with respect to the ambient atmosphere.

3. The device of claim 1, wherein the controller is further configured to hold the port in an open position for a first time to allow the gripping device to introduce or withdraw the one or more sample containers, and to close the port for times other than the first time.

4. The device of claim 1, wherein an outer periphery of the port has a rubber seal and an outer diameter of the gripping device is sized to provide an air-tight seal when the gripping device is at least partially inserted therethrough.

5. The device of claim 1, wherein the gripping device includes a flange, the flange being configured to seal against the port when the gripping device is at least partially inserted therethrough.

6. The device of claim 1, wherein the gripping device is substantially cylindrical in shape.

7. The device of claim 1, wherein the plurality of sample containers are supported on a platform housed in the chamber.

8. The device of claim 7, wherein the platform is a rotatable carousel rotatably mounted within the chamber.

9. The device of claim 1, wherein the thermal cycling is configured for nucleic acid amplification.

10. The device of claim 1, wherein the plurality of sample containers are configured for relatively rapid thermal equilibration and to allow for detection of the reaction mixture.

11. The device of claim 1, wherein the plurality of sample containers are formed from glass or plastic materials or a combination thereof.

12. The device of claim 1, wherein a plurality of connected sample containers may be introduced to or withdrawn from the chamber simultaneously.

13. The device of claim 12, wherein the plurality of connected sample containers form part of a clip.

14. The device of claim 12, wherein the plurality of connected sample containers include five individual sample containers.

15. The device of claim 1, further comprising:
 an elevating device,
 wherein the elevating device is adapted for at least partially elevating the one or more selected sample containers thereby enabling the gripping device to grip the one or more selected sample containers.

16. The device of claim 1, wherein the sample containers are tubes.

17. The device of claim 1, wherein the selectively openable port in the open position defines an aperture of between 20 mm to 30 mm in diameter.

18. The device of claim 15, wherein the elevating device comprises a push pin means for partially elevating the one or more selected sample containers.

19. The device of claim 15, further comprising:
 at least one chamber cooling port,
wherein the at least one chamber cooling port comprises a closed or open position.

20. The device of claim 8, wherein said controller is further configured to rotate said carousel during cycling to apply centrifugal force to said sample containers during cycling for maintaining the reaction mixture at the base of said sample containers.

21. The device of claim 1, wherein the gripping device introduces or withdraws the one or more selected sample containers from the chamber in a substantially axial motion with respect to the sample container.

* * * * *